United States Patent [19]

Hinsken et al.

[11] 4,284,790
[45] Aug. 18, 1981

[54] 3-HYDROXYBENZYL COMPOUNDS USEFUL AS ANTIOXIDANTS

[75] Inventors: Hans Hinsken, Lörrach, Fed. Rep. of Germany; Horst Mayerhoefer, Oberwil; Wolfgang Mueller, Allschwil, both of Switzerland

[73] Assignee: Sandoz Ltd., Basel, Switzerland

[21] Appl. No.: 5,758

[22] Filed: Jan. 23, 1979

[30] Foreign Application Priority Data

Jan. 27, 1978 [CH] Switzerland ............... 926/78
Feb. 2, 1978 [CH] Switzerland ............. 1137/78

[51] Int. Cl.³ ............... C07C 149/40; C07C 149/41; C08K 5/13; C08K 5/37
[52] U.S. Cl. .................... 560/15; 252/402; 252/403; 252/404; 260/45.8 NT; 260/45.85 A; 260/45.85 B; 260/45.85 P; 260/45.85 T; 260/45.9 NC; 544/197; 560/10; 560/16; 560/56; 560/59; 560/60; 560/85; 560/193; 564/156; 564/160
[58] Field of Search ............. 560/15, 10, 16, 56, 560/59, 60

[56] References Cited

U.S. PATENT DOCUMENTS

| 2,724,721 | 11/1955 | Reiner | 560/15 |
| 3,277,148 | 10/1966 | Steinberg | 560/15 |
| 3,465,029 | 9/1969 | Beirne | 560/15 |
| 3,538,047 | 11/1970 | Brans | 560/15 |
| 3,546,272 | 8/1970 | Brans | 560/15 |
| 3,637,802 | 1/1972 | Eggensperger | 560/15 |
| 3,637,809 | 1/1972 | Kleiner | 560/15 |
| 3,699,152 | 10/1972 | Hechnbleikner | 560/15 |
| 3,810,869 | 5/1974 | Zaweski | 560/15 |
| 4,021,468 | 5/1977 | Lind | 560/15 |
| 4,134,879 | 1/1979 | Schmidt | 560/15 |

FOREIGN PATENT DOCUMENTS 1255610 12/1971 United Kingdom .

OTHER PUBLICATIONS

Weylor, Nakromol, Chemie, 9 pp. 16, 21 & 22 (1953).

Primary Examiner—Howard T. Mars
Assistant Examiner—Michael Shippen
Attorney, Agent, or Firm—Gerald D. Sharkin; Richard E. Vila; Joseph J. Borovian

[57] ABSTRACT

3-Hydroxylbenzyl compounds of formula,

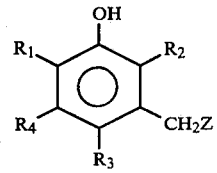

in which each of $R_1$, $R_2$ and $R_3$ is a hydrocarbon group, e.g. alkyl, $R_4$ is hydrogen or alkyl, or forms with $R_1$ —$CH_2CH_2CH_2CH_2$—, and Z is either an oxygen- or sulphur-containing group featuring at least one ester or amide moiety, or a disubstituted amino group, Z being bound to the rest of the molecule via the oxygen or sulphur atom, or nitrogen atom, respectively, are useful as antioxidants. Organic materials which are susceptible to the degradative effects of oxygen are treated with one or more of such compounds, e.g. by incorporation into the body of the organic material, in order to be stabilized against such effects.

6 Claims, No Drawings

3-HYDROXYBENZYL COMPOUNDS USEFUL AS ANTIOXIDANTS

The present invention relates to 3-hydroxybenzyl compounds which are useful as antioxidants.

More particularly, the present invention provides compounds of formula I,

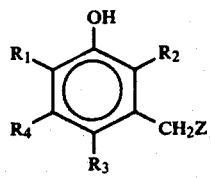

in which either
$R_1$ is $(C_{1-18})$alkyl, $(C_{5-8})$cycloalkyl, $(C_{1-5})$-alkyl-$(C_{5-8})$cycloalkyl having an aggregate of carbon atoms not exceeding 10, or phenyl, and
$R_4$ is hydrogen or $(C_{1-4})$alkyl, or $R_1$ and $R_4$ together form —$CH_2CH_2CH_2CH_2$—,
each of $R_2$ and $R_3$, independently, is $(C_{1-4})$alkyl or cyclohexyl, with the proviso that both $R_2$ and $R_3$ cannot be cyclohexyl, and
Z is a group (b) or (c),

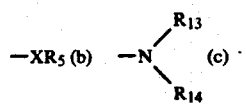

in which
X is oxygen or sulphur,
$R_5$ is a group (d) or (e),

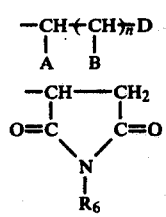

A is hydrogen, $(C_{1-4})$alkyl, phenyl, or

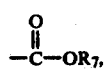

B is hydrogen, methyl, hydroxyl or

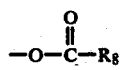

with the proviso that B cannot be methyl when A is other than hydrogen,
D is

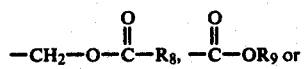

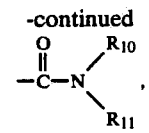

n is zero or an integer 1 to 21, with the proviso that when B in the group (d) is other than hydrogen, then n is exclusively 1,
$R_6$ is $(C_{1-8})$alkyl; phenyl-$(C_{1-4})$-alkyl; or phenyl, unsubstituted or substituted with one or two $(C_{1-4})$alkyl groups,
$R_7$ is $(C_{1-18})$alkyl; $(C_{5-8})$cycloalkyl; phenyl-$(C_{1-4})$alkyl; phenyl, unsubstituted or substituted with one or two $(C_{1-4})$ alkyl groups; or a group (a),

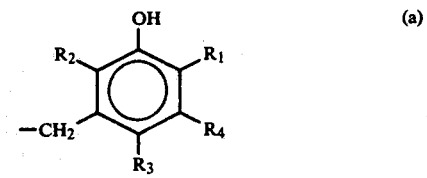

$R_8$ is $(C_{1-18})$alkyl, $(C_{5-8})$cycloalkyl, phenyl-$(C_{1-4})$alkyl or phenyl,
$R_9$ is $(C_{1-18})$alkyl; $(C_{5-8})$cycloalkyl; phenyl-$(C_{1-4})$alkyl; phenyl, unsubstituted or substituted with one or two $(C_{1-4})$alkyl groups; or a group (a), as defined above, (f), (g), (h), (i) or (j),

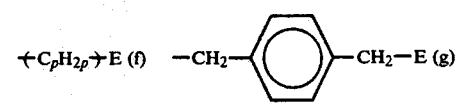

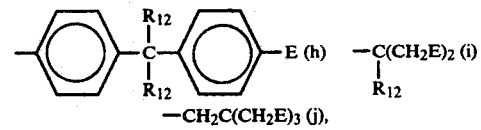

$R_{10}$ is hydrogen; $(C_{1-18})$alkyl; $(C_{5-8})$cycloalkyl; benzyl; or phenyl, unsubstituted or substituted with one or two $(C_{1-4})$alkyl groups,
$R_{11}$ is $(C_{1-8})$alkyl or phenyl,
p is an integer 2 to 21,
E is a group (k),

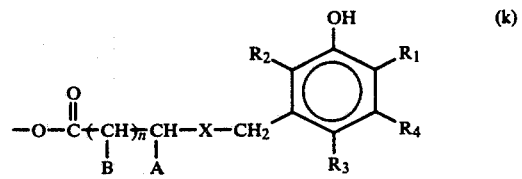

with the proviso that when B in the group (k) is other than hydrogen, then n is exclusively 1,
$R_{12}$ is hydrogen or $(C_{1-6})$alkyl, either
$R_{13}$ is $(C_{1-24})$alkyl, phenyl, $(C_{1-12})$-alkyl-phenyl or a group (l) or (m),

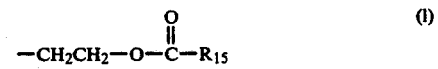

-continued

and $R_{14}$ is $(C_{1-24})$alkyl, phenyl, $(C_{1-12})$alkyl-phenyl, a group (l), as defined above, or a group (n), (o), (p) or (q),

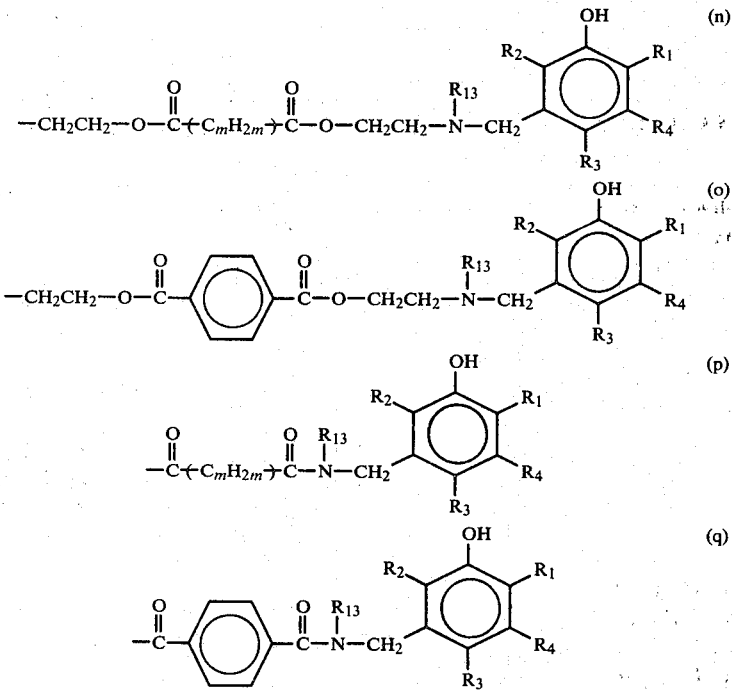

or $R_{13}$ is $(C_{1-18})$alkyl; phenyl, unsubstituted or substituted with one or two $(C_{1-4})$alkyl groups; or a group (l), and $R_{14}$ is a group (r),

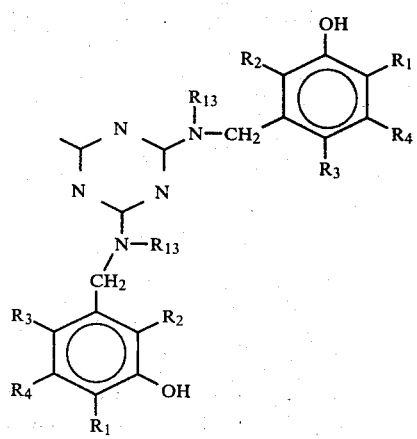

$R_{15}$ is $(C_{1-24})$alkyl, phenyl or phenyl-$(C_{1-9})$alkyl, and m is zero or an integer 1 to 21, with the further provisos:

(i) that when any symbol $R_1$, $R_2$, $R_3$, $R_4$, X, $R_8$, $R_{13}$ or $R_{15}$ occurs more than once in the molecule, then each such symbol has a meaning independently from any other such symbol, (ii) that when any X is oxygen, then A attached to the carbon atom adjacent to such X cannot be hydrogen, (iii) that when A is —COOR$_7$, then B can only be hydrogen, n can only be 1, and D can only be —COOR$_9$, in which $R_9$ is other than a group (f), (g), (h), (i) or (j); or —CONR$_{10}$R$_{11}$, (iv) that when B is hydroxyl or —OCOR$_8$, then A can only be hydrogen and D can only be —CH$_2$OCOR$_8$, (v) that when D is —COOR$_9$ and $R_9$ is a group (f), (g), (h), (i) or (j), then A can only be hydrogen, $(C_{1-4})$alkyl or phenyl, B can only be hydrogen or, when A is hydrogen, alternatively methyl, and each A, B and n has the same meaning as each other A, B and n, respectively, and (vi) that when $R_{13}$ in the group (c) is a group (m), then $R_{14}$ cannot be a group (p) or (q).

In the above definition, "phenyl" means unsubstituted phenyl unless otherwise indicated. Any alkyl or alkylene group may be straight or branched chain.

When any $R_1$ is alkyl, this is preferably $(C_{1-4})$alkyl, more preferably tert.-butyl. The preferred cycloalkyl or alkyl-cycloalkyl for any $R_1$ when signifying such a group is cyclohexyl or 1-methylcyclohexyl, respectively.

Of all the significances of any $R_1$, alkyl, alkylcycloalkyl and phenyl are preferred, and alkyl is most preferred.

When any $R_2$ or $R_3$ is alkyl, this is preferably methyl. Of both significances of $R_2$ or $R_3$, alkyl is preferred.

When any $R_4$ is alkyl, this is preferably methyl. Of all the significances of any $R_4$, hydrogen and alkyl are preferred, and hydrogen is most preferred.

Any X is preferably sulphur.

$R_5$ is preferably a group (d), more preferably of formula

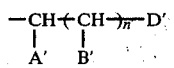

in which A', B', D' and n' are as defined hereinafter.

When A in any group (d) or (k) is alkyl, this is preferably methyl. $R_7$ as alkyl in the group —COOR$_7$, as one of the meanings of A in the group (d), is preferably $(C_{8-18})$alkyl, more preferably $(C_{12-18})$alkyl, and most preferably $C_{14}$, $C_{16}$, $C_{17}$ or $C_{18}$alkyl. When $R_7$ is cycloalkyl or phenylalkyl, this is preferably cyclohexyl or benzyl, respectively. When $R_7$ is unsubstituted or substituted phenyl, this is preferably unsubstituted phenyl. Finally, when $R_7$ is a group (a), this is preferably a group (a'), i.e. of formula,

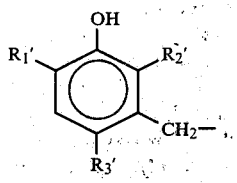

in which each of $R_1'$, $R_2'$ and $R_3'$, independently, is $(C_{1-4})$alkyl.

Of all the significances of $R_7$, alkyl, unsubstituted and substituted phenyl, and a group (a) are preferred, alkyl and a group (a) are more preferred, and alkyl is most preferred.

In the group (d) in which D is other than the group —COOR$_9$ in which $R_9$ is a group (f), (g), (h), (i) or (j), A is preferably hydrogen or a group —COOR$_7$, especially hydrogen or a group —COOR$_7'$, in which $R_7'$ is $(C_{12-18})$alkyl or a group (a'). When, however, D is the group —COOR$_9$ in which $R_9$ is a group (f), (g), (h), (i) or (j), A is preferably hydrogen.

When B or D, independently, in the group (d) is the group —OCOR$_8$ or —CH$_2$OCOR$_8$, respectively, $R_8$, as alkyl, is preferably $(C_{4-18})$alkyl, more preferably $(C_{8-18})$alkyl, and most preferably $(C_{7-17})$alkyl. When $R_8$ is cycloalkyl or phenylalkyl, this is preferably cyclohexyl or benzyl, respectively. Of all the significances of $R_8$, alkyl and phenyl are preferred, and alkyl is most preferred.

In the group (d) in which D is the group —CH$_2$OCOR$_8$, B is preferably hydrogen or a group —OCOR$_8$, and most preferably a group —OCOR$_8$. When, however, D is the group —COOR$_9$ or —CONR$_{10}$R$_{11}$, B is preferably hydrogen.

When D in the group (d) is the group —COOR$_9$, $R_9$, as alkyl, is preferably $(C_{8-18})$alkyl, more preferably $(C_{12-18})$ alkyl, and most preferably $C_{14}$, $C_{16}$, $C_{17}$ or $C_{18}$ alkyl. When $R_9$ is cycloalkyl or phenylalkyl, this is preferably cyclohexyl or benzyl, respectively. When $R_9$ is unsubstituted or substituted phenyl, this is preferably unsubstituted phenyl.

p in the group (f) is preferably 2 to 12, and more preferably 2, 4, 6, 8, 10 or 12. In the group (f), the moiety —C$_p$H$_{2p}$— can be straight or branched chain alkylene, but is preferably straight chain alkylene.

$R_{12}$ in the group (h) or (i) is preferably $(C_{1-6})$ alkyl, more preferably $(C_{1-4})$alkyl.

n in the group (d) or (k) is preferably zero or 1.

Of all the significances of $R_9$, alkyl, unsubstituted or substituted phenyl and the groups (a), (f), (h), (i) and (j) are preferred, alkyl and the groups (a), (f), (h), (i) and (j) are more preferred, especially $R_9'$ as hereinafter defined, and alkyl and the group (j) are most preferred.

When D in the group (d) is the group —CONR$_{10}$R$_{11}$, $R_{10}$, as alkyl, is preferably $(C_{8-18})$alkyl. When $R_{10}$ is cycloalkyl or unsubstituted or substituted phenyl, this is preferably cyclohexyl or unsubstituted phenyl, respectively. $R_{11}$, as alkyl, is preferably $(C_{1-4})$alkyl. Of all the significances of $R_{10}$, hydrogen, alkyl and unsubstituted or substituted phenyl are preferred, hydrogen and alkyl are more preferred, and hydrogen is most preferred. $R_{11}$ is preferably alkyl.

Of all the significances of D, the groups —CH$_2$OCOR$_8$ and —COOR$_9$ are preferred, especially the groups —CH$_2$OCOR$_8'$ and —COOR$_9'$, as hereinafter defined.

When $R_6$ in the group (e) is alkyl, this is preferably $(C_{1-4})$alkyl, and most preferably methyl. When it is phenylalkyl or unsubstituted or substituted phenyl, it is preferably benzyl or unsubstituted phenyl, respectively. Of all the significances of $R_6$, alkyl and unsubstituted or substituted phenyl are preferred, and alkyl is most preferred.

In the compounds of formula I in which $R_{14}$ is other than a group (r), each of $R_{13}$ and $R_{14}$, independently, as alkyl, is preferably $(C_{1-18})$alkyl.

When both $R_{13}$ and $R_{14}$ are alkyl, then the total carbon atoms contained by $R_{13}$ and $R_{14}$ is preferably at least 6, more preferably at least 12, and most preferably at least 18. Furthermore, when $R_{13}$ is a group (l) or (m), and $R_{14}$ is alkyl, then this alkyl is preferably $(C_{1-8})$alkyl, more preferably $(C_{1-4})$alkyl, and most preferably methyl, and, similarly, when $R_{14}$ is a group (l), (n), (o), (p) or (q), and $R_{13}$ is alkyl then this alkyl preferably is $(C_{1-8})$alkyl, more preferably $(C_{1-4})$alkyl, and most preferably methyl.

When $R_{13}$ is a group (l) or (m), or $R_{14}$ is a group (l), $R_{15}$ in such a group is preferably alkyl, more preferably $(C_{8-18})$alkyl. The moiety —C$_m$H$_{2m}$— in the group (n) or (p) can be straight or branched chain alkylene, but is preferably straight chain alkylene. m therein is preferably an integer 1 to 12, more preferably 2, 6, 8, 10 or 12.

Of all the significances of $R_{13}$ in such compounds, alkyl, the group (l) and the group (m) are preferred, especially $(C_{1-18})$alkyl, —CH$_2$CH$_2$OCOR$_{15}'$, and —COR$_{15}'$ in which $R_{15}'$ is $(C_{8-18})$alkyl. Of all the significances of $R_{14}$, alkyl and the groups (l), (n), (o), (p) and (q) are preferred, especially $(C_{1-18})$alkyl and the groups (l'), (n'), (o'), (p') and (q'), as hereinafter defined.

In the compounds of formula I in which $R_{14}$ is the group (r), $R_{13}$, as alkyl, is preferably $(C_{1-4})$alkyl and most preferably methyl. Of all the significances of $R_{13}$ in such compounds, alkyl is preferred.

In the compounds of formula I in which Z is a group (c), there is preferably at least one of the (l), (m), (n), (o), (p) and (q) groups present.

In general, when any symbol $R_1$, $R_2$, $R_3$, $R_4$, X, $R_8$, $R_{13}$ or $R_{15}$ occurs more than once in the molecule, then each such symbol preferably has the same meaning. Thus, for example, when more than one group (a) occurs in the molecule, then the groups (a) are preferably identical.

Of the compounds of formula I, a particular class is constituted by those compounds of formula I in which $R_1$, $R_2$, $R_3$ and $R_4$ are as defined above and Z is a group $(b_a)$, $$-XR_{5a} \qquad (b_a)$$

in which X is oxygen or sulphur,
$R_{5a}$ is a group ($d_a$) or ($e_a$),

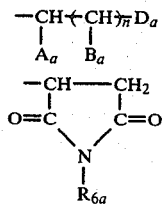

$A_a$ is hydrogen or

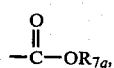

$B_a$ is hydrogen, hydroxyl or

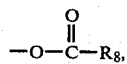

$D_a$ is

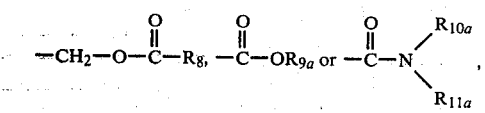

n is zero or an integer 1 to 21, with the proviso that when $B_a$ in the group $d_a$ is other than hydrogen, then n is exclusively 1, $R_{6a}$ is ($C_{1-8}$)alkyl, phenyl-($C_{1-4}$)alkyl, or phenyl,
$R_{7a}$ is ($C_{1-18}$)alkyl, ($C_{5-8}$)cycloalkyl, phenyl-($C_{1-4}$)alkyl, phenyl, or a group (a), as defined above,
$R_8$ is as defined above,
$R_{9a}$ is ($C_{1-18}$)alkyl, ($C_{5-8}$)cycloalkyl, phenyl-($C_{1-4}$)alkyl, phenyl, or a group (a), as defind above, ($f_a$), ($g_a$), ($i_a$), or ($j_a$),

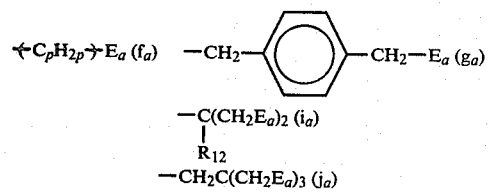

$R_{10a}$ is hydrogen, ($C_{1-18}$)alkyl, ($C_{5-8}$)cycloalkyl, benzyl or phenyl,
$R_{11a}$ is ($C_{1-8}$)alkyl,
p is an integer 2 to 21,
$E_a$ is a group ($k_a$)

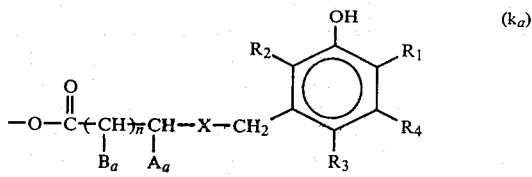

with the proviso that when $B_a$ in the group ($k_a$) is other than hydrogen, then n is exclusively 1, and $R_{12}$ is as defined above,
with the further provisos:
(i) that when any symbol $R_1$, $R_2$, $R_3$, $R_4$, X or $R_8$ occurs more than once in the molecule, then each such symbol has a meaning independently from any other such symbol,
(ii) that when any X is oxygen, then $A_a$ attached to the carbon atom adjacent to such X cannot be hydrogen,
(iii) that when $A_a$ is —$COOR_{7a}$, then $B_a$ can only be hydrogen, n can only be 1, and $D_a$ can only be —$COOR_{9a}$, in which $R_{9a}$ is other than a group ($f_a$), ($g_a$), ($i_a$) or ($j_a$); or —$CONR_{10}R_{11}$,
(iv) that when $B_a$ is hydroxyl or —$OCOR_8$, then $A_a$ can only be hydrogen and $D_a$ can only be —$CH_2OCOR_8$, and
(v) that when $D_a$ is —$COOR_{9a}$ and $R_{9a}$ is a group ($f_a$), ($g_a$), ($h_a$), ($i_a$) or ($j_a$), then $A_a$ and $B_a$ can only be hydrogen and X can only be sulphur.

A further particular class of the compounds of formula I is constituted by those compounds of formula I in which $R_1$, $R_2$, $R_3$ and $R_4$ are as defined above and Z is a group ($c_a$),

in which
$R_{13a}$ is ($C_{1-24}$)alkyl, phenyl, ($C_{1-12}$)alkylphenyl or a group (l) or (m), as defined above,
$R_{14a}$ is ($C_{1-18}$)alkyl, phenyl, ($C_{1-12}$)alkylphenyl, or a group (l), (o) or (q), as defined above, or a group ($n_a$) or ($p_a$),

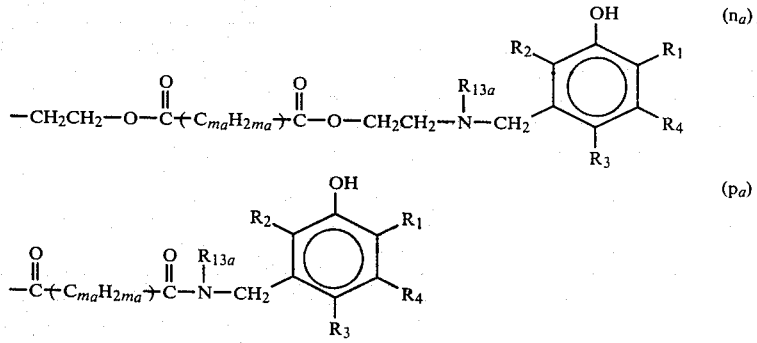

and $m_a$ is an integer 1 to 21,
with the further provisos:
(i) that when any symbol $R_1$; $R_2$; $R_3$; $R_4$; $R_{13}$ or $R_{13a}$; or $R_{15}$ occurs more than once, then each such symbol has the same meaning as any other such symbol, and
(ii) that when $R_{13a}$ is a group (m), then $R_{14a}$ cannot be a group ($p_a$) or (q).

A preferred class of compounds of formula I is constituted by the compounds of formula I',

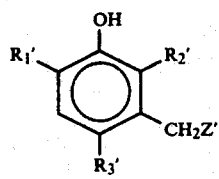     I' in which each of
$R_1'$, $R_2'$ and $R_3'$, independently, is $(C_{1-4})$-alkyl, and
Z' is a group (b') or (c'), —XR$_5'$    (b')

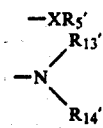    (c')

in which
X is oxygen or sulphur,
$R_5'$ is a group (d'),

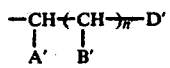    (d')

A' is hydrogen or

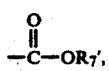

B' is hydrogen or

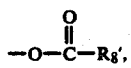

D' is

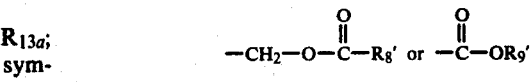

n' is zero or 1,
$R_7'$ is $(C_{12-18})$alkyl or a group (a'),

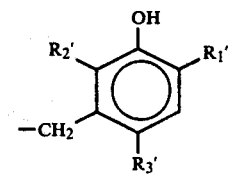    (a')

$R_8'$ is $(C_{4-18})$alkyl,
$R_9'$ is $(C_{12-18})$alkyl, or a group (a'), as defined above, (f'), (h'), (i') or (j'),

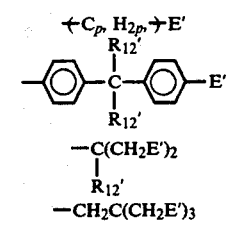

p' is an integer 2 to 12,
E' is a group (k'),

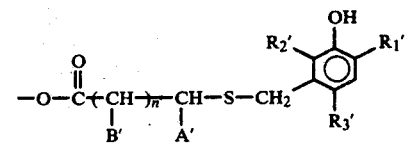    (k')

$R_{12}'$ is $(C_{1-4})$alkyl,
$R_{13}'$ is $(C_{1-18})$alkyl or a group (l') or (m'),

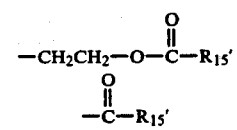

$R_{14}'$ is $(C_{1-18})$alkyl, a group (l'), as defined above, or a group (n'), (o'), (p') or (q'),

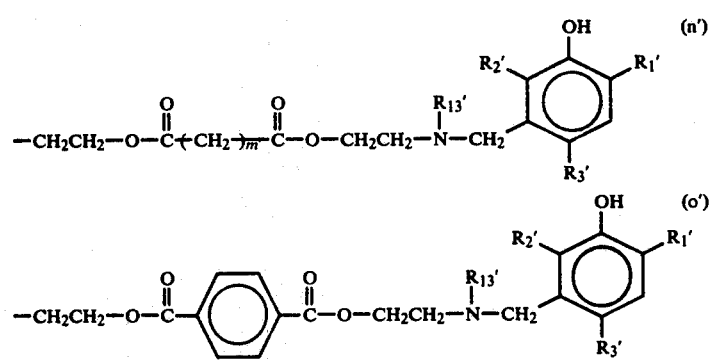

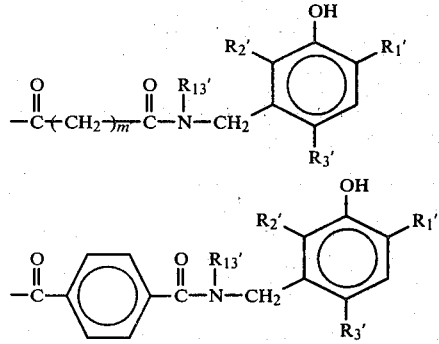

$R_{15}'$ is $(C_{8-18})$alkyl, and
$m'$ is an integer 1 to 12,
with the provisos:
(i) that when any symbol $R_1'$, $R_2'$, $R_3'$, X, $R_8'$, $R_{13}'$ or $R_{15}'$ occurs more than once in the molecule, then each such symbol has a meaning independently from any other such symbol,
(ii) that when X is oxygen, then A' can only be $-COOR_7'$,
(iii) that when A' is $-COOR_7'$, then B' can only be hydrogen, n' can only be 1 and D' can only be $-COOR_9'$, in which $R_9'$ is other than a group (f'), (h'), (i') or (j'),
(iv) that when B' is $-OCOR_8'$, then A' can only be hydrogen and D' can only be $-CH_2OCOR_8'$,
(v) that when D' is $-COOR_9'$ and $R_9'$ is a group (f'), (h'), (i'), or (j'), then A' and B' can only be hydrogen, and X can only be sulphur,
(vi) that when $R_{13}'$ in the group (c') is a group (m'), then $R_{14}'$ cannot be a group (p') or (q').

The present invention further provides a process for the production of those compounds of formula I in which Z is a group (b), comprising reacting a compound or, as appropriate, two or more compounds, of formula II,

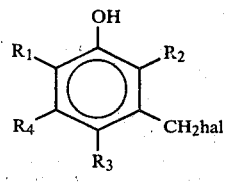

in which $R_1$, $R_2$, $R_3$ and $R_4$ are as defined above, and hal is chlorine or bromine,
with a compound of formula IIId or IIIe,

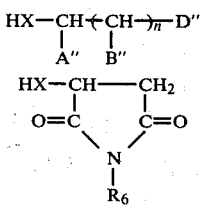

in which
X is oxygen or sulphur,
A" is A, as defined above, or $-COOH$,
B" is hydrogen, methyl or hydroxyl, with the proviso that B" cannot be methyl when A" is other than hydrogen, (p')

(q')

D" is

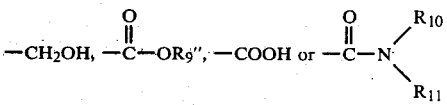

n is zero or an integer 1 to 21, with the proviso that when B" is other than hydrogen, then n is exclusively 1,
$R_6$ is as defined above,
$R_9''$ is $(C_{1-18})$alkyl; $(C_{5-8})$cycloalkyl; phenyl-$(C_{1-4})$alkyl; phenyl, unsubstituted or substituted with one or two $(C_{1-4})$alkyl groups; or a group (a), as defined above, (f"), (g"), (h"), (i") or (j"),

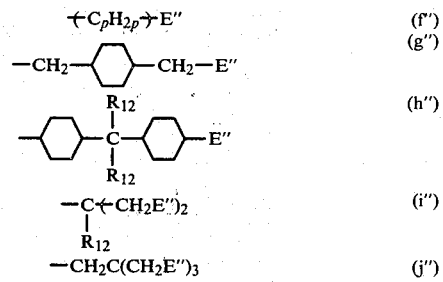

$R_{10}$, $R_{11}$, p and $R_{12}$ are as defined above, and E" is a group (k"),

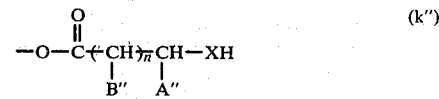

with the proviso that when B" in the group (k") is other than hydrogen, then n is exclusively 1,
and with the further provisos:
(i) that when A" is a group $-COOR_7$ in which $R_7$ is a group (a), then the $R_1$, $R_2$, $R_3$ and $R_4$ therein are independent from the $R_1$, $R_2$, $R_3$ and $R_4$, respectively, in the compound or mixture of compounds of formula II,
(ii) that when any X is oxygen, then A" attached to the carbon atom adjacent to such X cannot be hydrogen,
(iii) that when A" is $-COOR_7$ or $-COOH$, then B" can only be hydrogen, n can only be 1, and D" can only be $-COOR_9''$, in which $R_9''$ is other than a group (f"), (g"), (h"), (i") or (j"); $-COOH$; or $-CONR_{10}R_{11}$, (iv) that when B" is hydroxyl, then A" can only be hydrogen and D" can only be —CH₂OH, and (v) that when D" is —COOR₉" and R₉" is a group (f"), (g"), (h"), (i") or (j"), then A" can only be hydrogen, (C₁₋₄)alkyl or phenyl, B" can only be hydrogen or, when A" is hydrogen, alternatively methyl, and each A", B" and n has the same meaning as each other A", B" and n, respectively, and, when A" is —COOH and/or D" is —COOH, esterifying the product with a compound of formula IV,

R₇OH    IV in which R₇ is as defined above, and/or with a compound of formula V,

R₉'''OH    V in which R₉''' has the above meanings given for R₉ except a group (f), (g), (h), (i) or (j), respectively, and, when B" is hydroxyl and/or D" is —CH₂OH and the compound of formula I in which B and/or D are/is —OCOR₈ and/or —CH₂OCOR₈, respectively, is required, esterifying the product with a compound or, as appropriate, two compounds, of formula VI,

R₈COOH    VI in which R₈ is as defined above, or a functional derivative thereof.

Those compounds of formula I in which Z is a group (b), wherein R₅ is a group (d) in which B is hydrogen or methyl, D is —COOR₉ in which R₉ is other than a group (f), (g), (h), (i), or (j), and n is 1 may alternatively be produced by reacting a compound of formula VII,

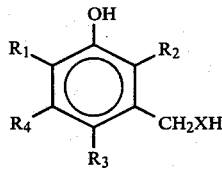

in which R₁, R₂, R₃, R₄ and X are as defined above, with a compound of formula VIII,

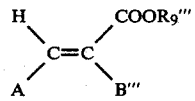

in which
A and R₉''' are as defined above, and
B''' is hydrogen, or, when A is hydrogen, methyl, and this process is also provided by the present invention.

The present invention further provides a process for the production of those compounds of formula I in which Z is a group (c), wherein R₁₄ is other than a group (n), (o), (p), (q) or (r), comprising reacting a compound of formula II, as defined above, with a compound of formula IX,

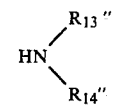

in which
R₁₃" is hydrogen, (C₁₋₂₄)alkyl, phenyl, (C₁₋₁₂)alkylphenyl or —CH₂CH₂OH, and
R₁₄" is (C₁₋₂₄)alkyl, phenyl (C₁₋₁₂)alkylphenyl or —CH₂CH₂OH,
and, when R"₁₃ is hydrogen, acylating the product with a compound of formula X,

R₁₅COOH    X in which R₁₅ is as defined above, or a functional derivative thereof, and, when R₁₃" and/or R₁₄" is/are —CH₂CH₂OH, esterifying the product with one or two compounds, as appropriate, of formula X, as defined above, or a functional derivative thereof.

Those compounds of formula I in which Z is a group (c), wherein R₁₄ is a group (n) or (o), may be produced by reacting a compound of formula XI or XII, respectively, HOOC—C_mH_{2m})COOH    XI

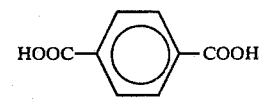

in which m is as defined above, or a functional derivative thereof, with one or two compounds, as appropriate, of formula XIII,

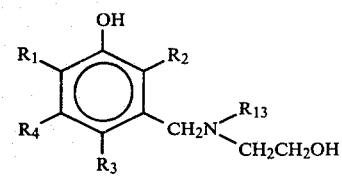

in which R₁, R₂, R₃, R₄ and R₁₃ are as defined above.
This process is also provided by the present invention.

Those compounds of formula I in which Z is a group (c), wherein R₁₄ is a group (p) or (q), may be produced by reacting a compound of formula XI or XII, respectively, as defined above, or a functional derivative thereof, with one or two compounds, as appropriate, of formula XIV,

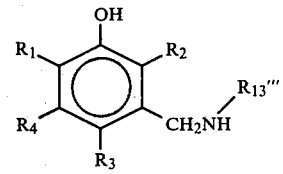

in which
R₁, R₂, R₃, R₄ are as defined above, and
R₁₃''' is (C₁₋₂₄)alkyl, phenyl, (C₁₋₁₂)alkyl-phenyl or —CH₂CH₂OH, and, when one or both $R_{13}''''$'s in the product is/are —$CH_2CH_2OH$, esterifying the product with one or two compounds, as appropriate, of formula X, as defined above, or a functional derivative thereof. This process is also provided by the present invention.

Finally, those compounds of formula I in which Z is a group (c), wherein $R_{14}$ is a group (r), may be produced by reacting a cyanuro halide of formula XV,

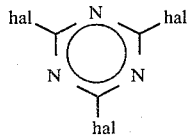  XV in which hal is chlorine or bromine, with one, two or three compounds, as appropriate, of formula XVI,

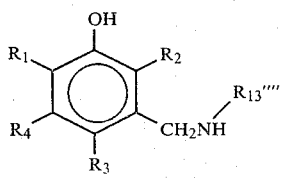  XVI in which
$R_1$, $R_2$, $R_3$ and $R_4$ are as defined above, and
$R_{13}''''$ is $(C_{1-18})$alkyl; phenyl, unsubstituted or substituted with one or two $(C_{1-4})$alkyl groups; or —$CH_2CH_2OH$,
and when one, two or all three $R_{13}''''$'s is/are -$CH_2CH_2OH$, esterifying the product with up to three compounds, as appropriate, of formula X, as defined above, or a functional derivative thereof. This process is also provided by the present invention.

In the above process definitions, the preferred functional derivatives of any compound of formula VI, X, XI or XII are the acid chloride and an ester, e.g. the methyl or ethyl ester. In general, the reaction conditions are standard, being known from analogous reactions of the same type, i.e. hydrogen halide elimination, esterification, Michael addition or acylation reactions, as appropriate. The intermediates of formula II to XVI are either known or can be produced in analogous manner to the known compounds from available starting materials.

The present invention further provides a method of stabilizing an organic material susceptible to the degradative effects of oxygen against such effects comprising treating said material with a stabilizing-effective amount of one or more compounds of formula I, as defined above. By the term treating, as used herein, is meant either incorporating into the body of the organic material, or surface coating the organic material, e.g. in a manner known per se, of which the former mode of treating is preferred for the preferred organic materials to be treated, i.e. polymeric organic materials.

Suitable organic materials which are stabilized by the method of the present invention include such plastics materials as polyolefins, e.g. polyethylene and polypropylene, polystyrene, polyesters, polymethyl methacrylates, polyphenylene oxides, polyurethanes, polyamides, e.g. nylon, polypropylene oxide, polyacrylonitrile, copolymers and terpolymers of the aforementioned polymers, polypyrrolidone, and such natural materials as natural rubber.

The compounds of the present invention are especially suitable for stabilizing polyethylene, polypropylene, polyesters, polyurethanes, polyamides, polyacrylonitrile, copolymers of styrene and acrylonitrile and of styrene and butadiene, and terpolymers of acrylonitrile, butadiene and styrene (ABS) and of acrylic ester, styrene and acrylonitrile, more particularly polyethylene, polypropylene and (ABS) terpolymers.

According to an embodiment of the method of the present invention, the compound of formula I is intimately mixed with a plastics material, e.g. polypropylene, preferably in particulate (granulate) form and in a kneader or other suitable mixing device, or in the melt, to obtain even distribution of the compound in the substrate. The treated material may then be formed into final shape, e.g. by extrusion to form, e.g. films, tubings or fibers. Of these two preferred mixing methods, that involving intimate mixing of the plastics material in particulate form and in a kneader or other suitable mixing device is preferred.

The polymeric organic materials need not necessarily be in the final polymerized or condensed form before being treated with the compounds of the present invention. Thus, according to a second embodiment of the method of the present invention, particularly suited to the stabilization of polymeric or copolymeric materials, the compound of formula I is mixed with the appropriate monomer or prepolymer and/or precondensate before polymerization or condensation is effected.

The suitable amount of stabilizing compound or compounds of formula I employed in the method of the present invention will naturally depend on several factors, e.g. the mode of application, the particular compound employed and the nature of the organic material to be treated. However, when the compound is incorporated into the body of the organic material, satisfactory results are generally obtained when the amount of compound employed is in the range 0.01 to 5% of the weight of the organic material to be treated. Preferably, however, the amount is in the range 0.05 to 1%.

The organic materials may also be treated with other additives besides the compounds of formula I to improve their properties, e.g. other stabilizers or costabilizers against the degradative effects of oxygen, heat and/or ultraviolet light. Particularly preferred additives are stabilizing, sulphur-containing compounds such as distearyl thiodipropionate, dilauryl thiodipropionate and tetrakis-(methylene-3-dodecylthiopropionate)methane, and stabilizing, phosphorus-containing compounds such as trinonyl phenylphosphite, 4,9-distearyl-3,5,8,10-tetraoxa-diphosphaspiroundecane and tris-(2,4-di-tert.-butylphenyl)phosphite. The relative proportion by weight of the compound or compounds of formula I to such an additive or additives in the method of the present invention is preferably in the range 1:5 to 5:1, more preferably 1:3 to 3:1 and most preferably 2:1 to 1:2, respectively.

Instead of the above-mentioned stabilizing, sulphur- or phosphorus-containing compounds, sterically-hindered phenols may be used together with the compounds of formula I for treating the organic materials in the method of the present invention. Particularly preferred such sterically-hindered phenols are stearyl 4-hydroxy-3,5-di-tert.-butylphenyl propionate, tetrakis-[methylene-3(3',5'-di-tert.-butyl-4-hydroxyphenyl)propionato]methane, 1,3,3-tris(2-methyl-4-hydroxy-5-tert.-butylphenyl)butane and 2,2'-methylene-bis(4-methyl-6-tert.-butylphenol). The relative proportion by weight of ness, and the residue, a pale brown resinous solid, is subsequently purified by passage of its solution in 95:5 toluene/acetone through a silica gel column. Produced is the compound of formula

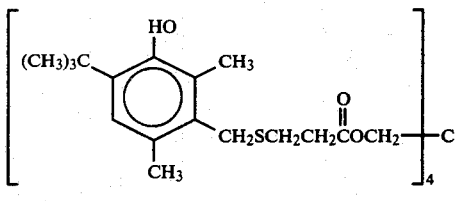

as a pale yellow, resinous solid.

EXAMPLE 5

By an analogous procedure to that described in Example 4 and using pentaerythritol-tetra-2-mercaptoacetate in place of pentaerythritol-3-mercaptopropionate, the compound of formula

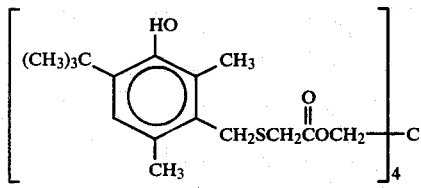

m.p. 182°–184°, is produced.

EXAMPLE 6

To a solution of 22.7 parts of 6-tert.-butyl-3-chloromethyl-2,4-xylenol and 5.3 parts of 3-mercaptopropionic acid in 35 parts of dimethylformamide are added dropwise, over a period of 40 minutes, 11.5 parts of triethylamine. During the addition the temperature is maintained by cooling within the range 30°–40°. Then the reaction mixture is warmed to 95° and stirred at this temperature for 15 minutes, after which the precipitate formed during the reaction is removed by filtration and the filtrate is evaporated under reduced pressure to dryness. The resulting reddish-brown, resinous residue is purified by passage of its solution in 10:1 benzene/methanol through a silica gel column and evaporation to dryness of the eluant. Produced is the compound of formula

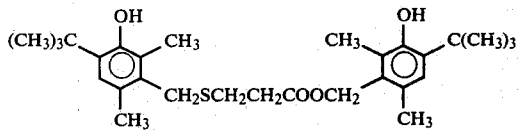

EXAMPLE 7

By an analogous procedure to that described in Example 6 and using mercaptomaleic acid in place of 3-mercaptopropionic acid, the compound of formula

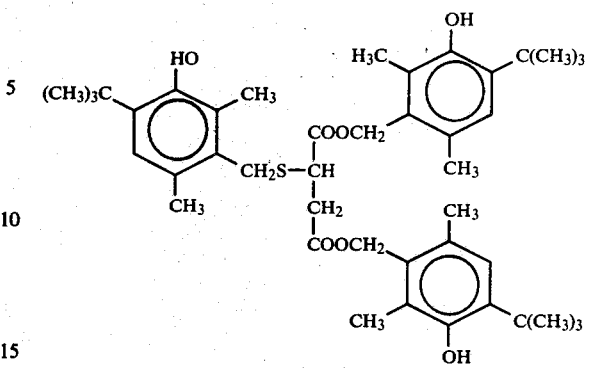

is produced.

EXAMPLE 8

A mixture of 5.6 g of 2,6-dimethyl-4-tert.-butyl-3-hydroxybenzyl mercaptan, 15.5 g of dioctadecyl maleate and 0.5 ml of triethylamine is heated to 100° C. and allowed to react over a period of five hours. Then the triethylamine is removed by evaporation at reduced pressure, and the residue is allowed to cool, affording 20.8 g of a yellow resin, m.p. 53°–54° with a strong, disagreeable smell.

The resin is warmed to 80° and air is passed through the resulting melt for 2 hours. After cooling to room temperature, the resulting solid is broken up into a beige powder (11.8 g), which is almost odorless.

This preparation is repeated, starting from 26.9 g of the mercaptan, 74.4 g of the maleate and 2.5 ml of triethylamine. There result 98 g of beige crystals, m.p. 53°–54°.

In both cases the compound of formula,

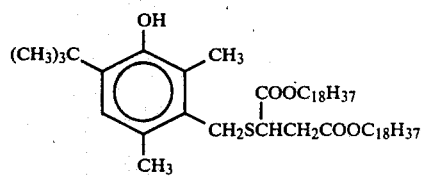

is produced.

EXAMPLES 9 AND 10

By an analogous procedure to that described in Example 8 and using dioctyl maleate and diethyl maleate, respectively, in place of dioctadecyl maleate, the following two compounds are produced:

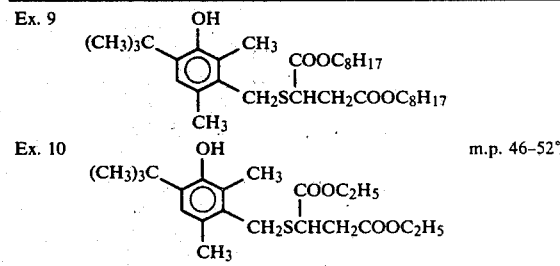

the compound or compounds of formula I to such an additive or additives in the method of the present invention is preferably in the range of 1:5 to 5:1 and more preferably 1:2 to 2:1, respectively.

The present invention further provides an organic material whenever treated according to the method of the present invention, as well any suitable composition containing one or more compounds of formula I, as defined above, for use in the method of the present invention. Such compositions, which may be referred to as master batches, preferably comprise 20 to 90% by weight of the compound, or mixture of compounds of formula I, more preferably 40 to 60% by weight, and a part of the substrate to be treated by the method of the present invention. The use of such a master batch in the method avoids the necessity for those practicing the method to initially make up the composition according to recommended ratio specifications before addition to the substrate to be stabilized. The master batch composition is readily worked into or applied onto the main body of the substrate by virtue of the presence of the same substrate in the master batch composition.

In the following Examples, which illustrate the present invention, the parts and percentages are by weight and the temperatures are in degrees Centigrade.

EXAMPLE 1

To a solution of 22.6 parts of 6-tert.-butyl-3-chloromethyl-2,4-xylenol and 10.8 parts of thioglycerol in 100 parts of dimethylformamide are added dropwise, over a period of 30 minutes, 10 parts of triethylamine. During the addition the reaction mixture reaches a temperature of 40°. The mixture is then stirred at 40° for 5 hours, after which the resulting precipitate is removed by filtration and the filtrate is concentrated by evaporation under reduced pressure to afford a pale yellow resin as the intermediate product.

6 parts of the resin produced in the previous stage are dissolved together with 3.3 parts of pyridine in 30 parts of chloroform. Then a solution of 12.4 parts of stearoyl chloride in chloroform is added dropwise to the solution at 0° to −10°. The mixture is allowed to react overnight, after which it is washed first with aqueous sodium bicarbonate solution and then with water. Finally, the organic phase is dried over Glauber's salt and subsequently evaporated to dryness. Produced is the compound, m.p. 32°–34°, of the formula

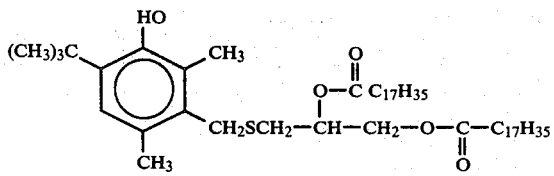

EXAMPLE 2

To a solution of 11.3 parts of 6-tert.-butyl-3-chloromethyl-2,4-xylenol and 5.3 parts of 3-mercaptopropionic acid in 35 parts of dimethylformamide are added dropwise, over a period of one hour, 10.1 parts of triethylamine. During the addition the temperature of the reaction mixture is maintained at 20° through cooling. Then the reaction mixture is heated to 60° and allowed to react for a further four hours with stirring. The solvent is thereafter removed by evaporation under reduced pressure, and the residue is dissolved in 60 parts of dilute hydrochloric acid and 71 parts of diethyl ether.

After being washed in turn with dilute hydrochloric acid, 10% aqueous sodium bicarbonate solution and water, the ethereal phase is dried over Glauber's salt and subsequently evaporated to dryness. In this way the intermediate of formula

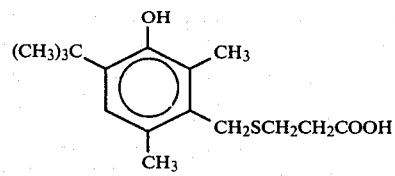

is produced.

The product of the previous stage (2.97 parts) and 2.70 parts 1-octadecanol are dissolved, together with a small quantity of p-toluenesulphonic acid, in 100 parts of toluene. On boiling the solution the calculated quantity of water is evolved, and after five hours reaction time the heating is terminated and the reaction mixture is allowed to cool to room temperature. Then the reaction solution is washed in turn with 10% aqueous sodium bicarbonate solution and water, and the organic phase is dried over Glauber's salt and evaporated under reduced pressure to dryness. On standing, the resulting pale yellow syrup gradually converts to a crystalline product, m.p. 44°–45°, which consists of the compound of formula

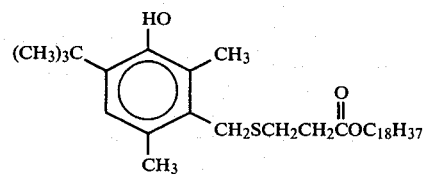

EXAMPLE 3

By an analogous procedure to that described in Example 2 and using 2-mercaptoacetic acid in place of 3-mercaptopropionic acid, the compound of formula

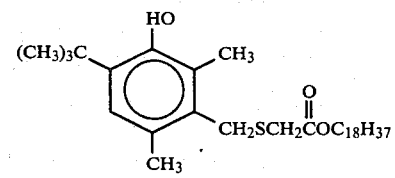

is produced.

EXAMPLE 4

To a solution of 11.33 parts of 6-tert.-butyl-3-chloromethyl-2,4-xylenol and 6.11 parts of pentaerythritoltetra-3-mercaptopropionate in 35 parts of dimethylformamide are added dropwise, over a period of 50 minutes, 5.1 parts of triethylamine. Then the reaction mixture is maintained at a temperature of 60° overnight. After evaporation of the solvent, the resulting residue is dissolved in 57 parts of diethyl ether and 50 parts of water, and the ethereal phase is washed in turn with 10% aqueous sodium bicarbonate solution and water and finally dried over Glauber's salt. The ethereal solution is then evaporated under reduced pressure to dry-

EXAMPLE 11

22.7 parts of 6-tert.-butyl-3-chloromethyl-2,4-xylenol and 26.2 parts of diethanolamine are dissolved in 100 parts of dimethylformamide. After a short time the temperature of the initially colorless solution has risen to about 35° and the color has changed to yellow. After 5 hours reaction time the reaction mixture is treated with water, precipitating a yellowish oil which slowly crystallizes. The colorless crystals are collected by filtration, washed with water and dried in vacuo. Produced is the intermediate, m.p. 93°–95°, of formula

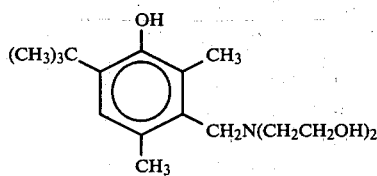

5.9 parts of the intermediate produced in the previous stage are dissolved together with 1.67 parts of pyridine in 30 parts of chloroform. Then a solution of 12.4 parts of stearoyl chloride in 37 parts of chloroform is added dropwise to the solution at −10°. The mixture is stirred for 15 hours at room temperature, after which the reaction mixture is washed first with aqueous sodium bicarbonate solution and then with water. Finally, the organic phase is dried over Glauber's salt and subsequently evaporated to dryness. Produced is a waxy product, m.p. 39°–42°, of the formula

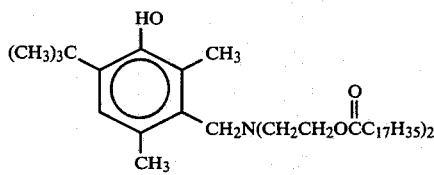

EXAMPLE 12

To 50 parts of ethanolamine is added dropwise over a period of 80 minutes a solution of 22.7 parts of 6-tert.-butyl-3-chloromethyl-2,4-xylenol in 50 parts of dimethylformamide. The mixture is then stirred at room temperature for 3 hours, and subsequently treated dropwise with water, whereupon a precipitate is formed. The precipitate is collected by filtration, washed with water and dried in vacuo. Produced are white crystals, m.p. 141°–143°, which consist of the compound of formula

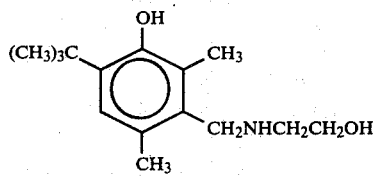

To a mixture of 5.03 parts of the compound produced as described in the previous stage, 30 parts of chloroform and 4.2 parts of triethylamine is added dropwise with cooling a solution of 12.44 parts of stearoyl chloride in 30 parts of chloroform. The temperature is maintained between 5° and 20° during the addition. Then the reaction mixture is stirred for 6 hours at room temperature and thereafter diluted by addition of 50 parts of chloroform. After washing the reaction mixture with three 50 parts quantities of water and drying the organic phase over Glauber's salt, the phase is concentrated by evaporation. On addition of about 200 parts of methanol to the concentrate, a white crystalline precipitate is produced. The crystals are collected by filtration and recrystallized from acetone to afford a product, m.p. 61.5°–65°, which consists of the compound of formula

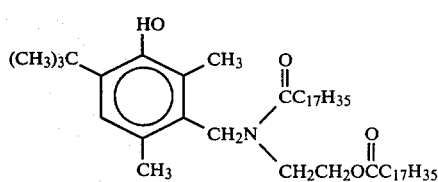

EXAMPLE 13

To a solution of 22.7 parts of 6-tert.-butyl-3-chloromethyl-2,4-xylenol in 100 parts of dimethylformamide are added dropwise over a period of 15 minutes 19 parts of 2-methylaminoethanol. The clear reaction mixture is then stirred at room temperature for 2 hours and thereafter poured into water, whereupon a crystalline precipitate is produced. The precipitate is washed with water and dried, and consists of the intermediate of formula

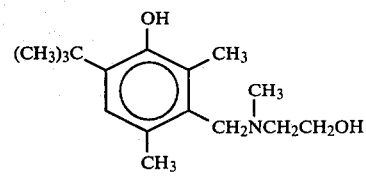

m.p. 77°–78.5°.

5.31 parts of the above intermediate are dissolved in 2.43 parts of triethylamine and 35 parts of chloroform. To the solution at 0° is added dropwise a solution of 2.03 parts of terephthalic acid dichloride in 25 parts of chloroform. The reaction mixture is then stirred overnight at room temperature and subsequently diluted by addition of 100 parts of chloroform. The reaction mixture is washed in turn with water, aqueous sodium bicarbonate solution and water, and the organic phase is then dried over Glauber's salt and evaporated to dryness. After purifying the resulting yellow resinous solid by passage of its solution in 4:1 toluene/acetone through a silica gel column and evaporation to dryness of the eluant, there is produced a crystalline product, m.p. 132°–133°, which consists of the compound of formula

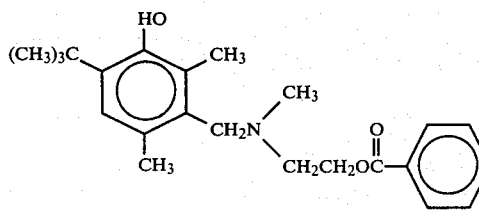 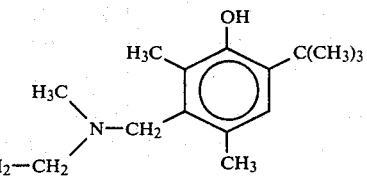

EXAMPLE 14

By an analogous procedure to that described in the first part of Example 13 and using dioctadecylamine in place of 2-methylaminoethanol, the compound of formula

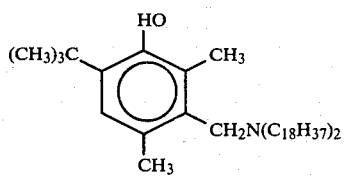

is produced.

EXAMPLE 15

By an analogous procedure to that described in the second part of Example 13 and using stearoyl chloride in place of terephthalic acid dichloride, the compound of formula

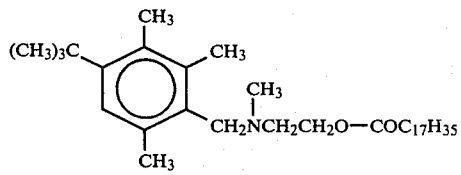

is produced.

EXAMPLE 16

To a mixture of 5.03 parts of 6-tert.-butyl-3-[N-(2-hydroxyethyl)aminomethyl]-2,4-xylenol (produced as described in the first part of Example 12) and 30 parts of chloroform is added dropwise over a period of 80 minutes a solution of 6.22 parts of stearoyl chloride in 30 parts of chloroform. During the addition the temperature of the reaction mixture is maintained under 20°. The reaction mixture is then stirred overnight at room temperature, whereafter it is diluted by addition of 100 parts of chloroform. After washing the reaction mixture in turn with water, aqueous sodium bicarbonate solution and water, the organic phase is dried over Glauber's salt and evaporated to dryness. The resulting off-white crystalline residue is recrystallized from methanol to afford colorless crystals, m.p. 115°–118°, consisting of the intermediate of formula

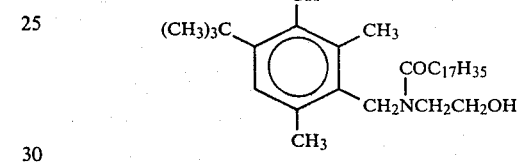

5.2 parts of the above intermediate and 1.02 parts of terephthalic acid dichloride are dissolved in 30 parts of chloroform. To the cooled solution are added dropwise 1.01 parts of triethylamine. After being stirred overnight at room temperature, the reaction mixture is diluted with 100 parts of chloroform. The chloroform solution is then washed in turn with water, aqueous sodium bicarbonate solution and water, dried over Glauber's salt and evaporated to dryness. Crystallization of the solid residue from acetone affords colorless crystals, m.p. 107°–109°, consisting of the compound of formula

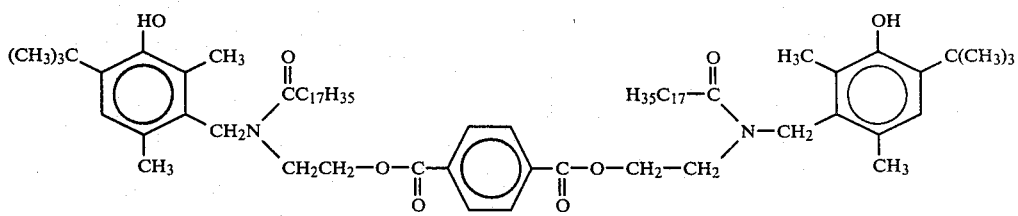

EXAMPLE 17 and 18

By an analogous procedure to that described in the first part of Example 16 and using 6-tert.-butyl-3-(N-methylaminomethyl)-2,4-xylenol (produced as described in the first part of Example 22) in place of 6-tert.-butyl-3-[N-(2-hydroxyethyl)aminomethyl]-2,4-xylenol and phthalic acid dichloride and sebacic acid dichloride, respectively, in place of stearoyl chloride, the following compounds, respectively, are produced:

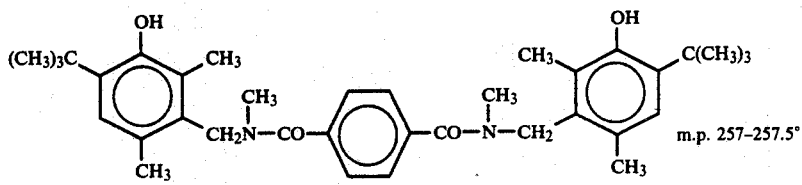
Ex. 17
m.p. 257-257.5°

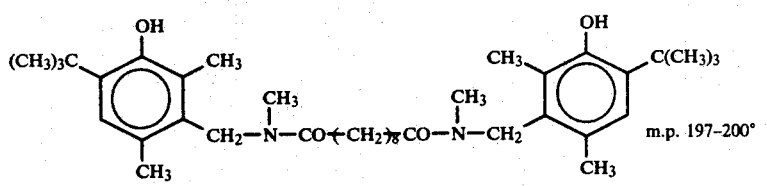
Ex. 18
m.p. 197-200°

EXAMPLES 19 and 20

By an analogous procedure to that described in the first part of Example 16 and using 6-tert.-butyl-3-(N-n-butylaminomethyl)-2,4-xylenol and 6-tert.-butyl-3-(N-n-dodecylaminomethyl)-2,4-xylenol, respectively, in place of 6-tert.butyl-3-[N-(2-hydroxyethyl)aminomethyl]-2,4-xylenol and phthalic acid dichloride in place of stearoyl chloride, the following compounds, respectively, are produced:

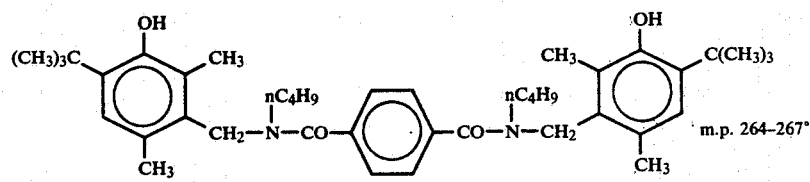
m.p. 264-267°

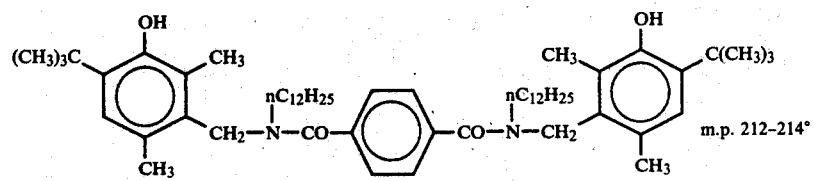
Ex. 20
m.p. 212-214°

EXAMPLE 21

By an analogous procedure to that described in the first part of Example 16 and using 6-tert.-butyl-3-(N-n-butylaminomethyl)-2,4-xylenol in place of 6-tert.-butyl-3[N-(2-hydroxyethyl)aminomethyl]-2,4-xylenol, the compound of formula m.p. 77-79°

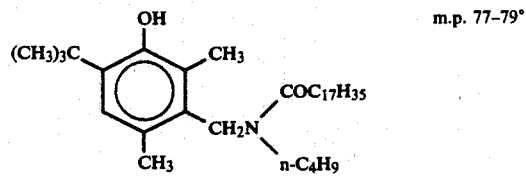

is produced.

EXAMPLE 22

To a mixture of 38.8 parts of a 40% aqueous solution of methylamine and 100 parts of dimethylformamide is added dropwise over a period of 45 minutes a solution of 11.3 parts of 6-tert.-butyl-3-chloromethyl-2,4-xylenol in 25 parts of dimethylformamide. The reaction mixture is then stirred for one hour and subsequently poured into 500 parts of water. Filtration of the resulting precipitate is followed by washing with water and drying in vacuo. Produced is a crystalline product, m.p. 176°-178°, which consists of the intermediate of formula

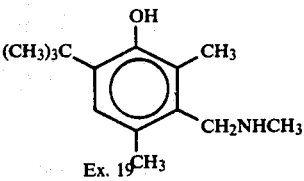
Ex. 19

To a mixture of 6.64 parts of the above intermediate, 2,4 parts of acetone and 1.59 parts of sodium carbonate is added dropwise a solution of 1.84 parts of cyanuro chloride in 20 parts of acetone. The mixture is then heated under reflux for 4 days. The resulting precipitate is removed by filtration and the filtrate is evaporated in vacuo to dryness. Purification of the residue is achieved by passage of its 10:3 toluene/methanol solution through a silica gel column and evaporation of the eluant in vacuo to dryness. Produced is a product, m.p. 137°-140°, which consists of the compound of formula

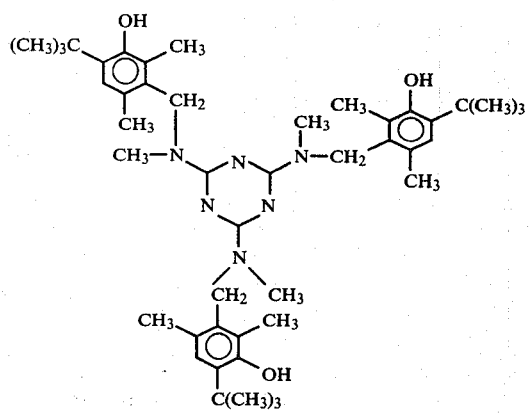

APPLICATION EXAMPLE 99.6 parts of unstabilized polypropylene powder (Profax 6501), 0.1 part of calcium stearate, 0.1 part of the compound produced as described in Example 1 and 0.2 parts of distearyl thiodipropionate are mixed together at 170° for 5 minutes using a laboratory rolling mill (Schwabenthan). From the resulting rolled sheet are produced 0.5 mm thick sample plates using a press (Bucher Guyer) at 230° under a pressure of 2 tons for 2 minutes and 30 tons for 3 minutes. The test plates are then submitted to an accelerated ageing test in a well aerated oven at 150°. The time taken for complete degradation of the polymer, recognizable by the grainy clouding of the test samples and a complete loss of mechanical stability, is measured for each test sample. The results indicate good activity for the tested stabilizing compound.

The remaining exemplified compounds are tested in an analogous manner.

What is claimed is:

1. A compound of the formula

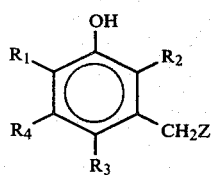

wherein $R_1$ is $C_{1-18}$ alkyl, $C_{5-8}$ cycloalkyl, $C_{1-5}$ alkyl-$C_{5-8}$ cycloalkyl having an aggregate of carbon atoms not exceeding 10, or unsubstituted phenyl, and $R_4$ is hydrogen or $C_{1-4}$ alkyl; or $R_1$ and $R_4$ together form $-CH_2CH_2CH_2CH_2-$; each of $R_2$ and $R_3$, independently, is $C_{1-4}$ alkyl or cyclohexyl, with the proviso that both $R_2$ and $R_3$ cannot be cyclohexyl; and Z is a group $-XR_5$ where X is oxygen or sulphur, and $R_5$ is a group

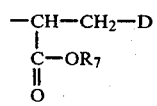

where D is

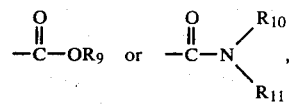

each of $R_7$ and $R_9$, independently, is $C_{1-18}$ alkyl, $C_{5-8}$ cycloalkyl, phenyl-$C_{1-4}$ alkyl, unsubstituted phenyl, phenyl monosubstituted by $C_{1-4}$ alkyl or phenyl disubstituted by $C_{1-4}$ alkyl, $R_{10}$ is hydrogen, $C_{1-18}$ alkyl, $C_{5-8}$ cycloalkyl, benzyl, unsubstituted phenyl, phenyl monosubstituted by $C_{1-4}$ alkyl or phenyl disubstituted by $C_{1-4}$ alkyl, and $R_{11}$ is $C_{1-8}$ alkyl or phenyl.

2. A compound according to claim 1, wherein Z is a group $-XR_{5a}$, where X is oxygen or sulphur and $R_{5a}$ is a group

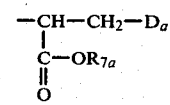

where $D_a$ is

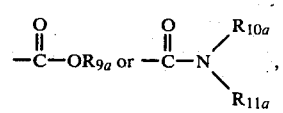

each of $R_{7a}$ and $R_{9a}$, independently, is $C_{1-18}$ alkyl, $C_{5-8}$ cycloalkyl, phenyl-$C_{1-4}$ alkyl or unsubstituted phenyl, $R_{10a}$ is hydrogen, $C_{1-18}$ alkyl, $C_{5-8}$ cycloalkyl, benzyl or unsubstituted phenyl, and $R_{11a}$ is $C_{1-8}$ alkyl.

3. A compound according to claim 1 having the formula

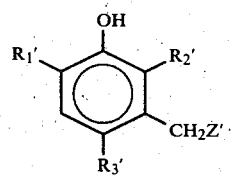

wherein each of $R_1'$, $R_2'$ and $R_3'$, independently, is $C_{1-4}$ alkyl; and $Z'$ is a group $-XR_5'$ where X is oxygen or sulphur, and $R_5'$ is a group

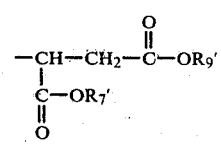

where each of $R_7'$ and $R_9'$, independently, is $C_{12-18}$ alkyl.

4. A compound according to claim 1, of formula,

6. A compound according to claim 1, of formula,
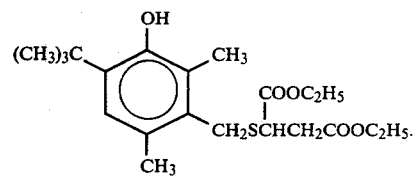
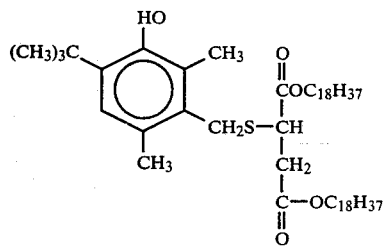
5. A compound according to claim 1, of formula,
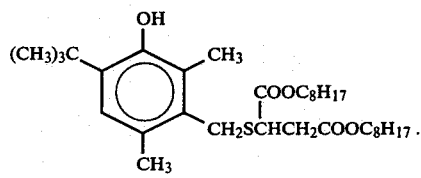
* * * * *

UNITED STATES PATENT AND TRADEMARK OFFICE
CERTIFICATE OF CORRECTION

PATENT NO. : 4,284,790

DATED : August 18, 1981

INVENTOR(S) : Hans Hinsken, et al.

It is certified that error appears in the above—identified patent and that said Letters Patent is hereby corrected as shown below:

Column 3, directly beneath line 43; delete the structural formula and substitute therefor

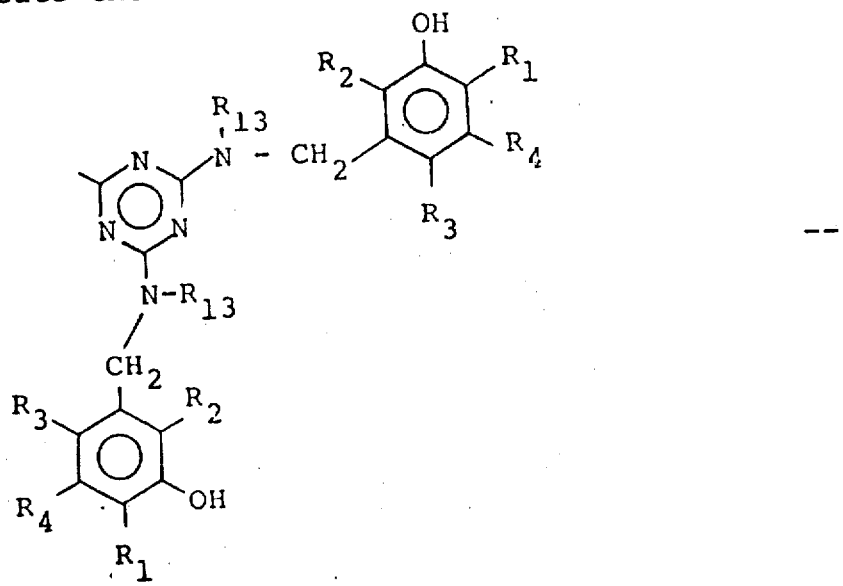

Column 12, directly beneath line 31; delete structural formula (g") and structural formula (h") and substitute therefor the formulae

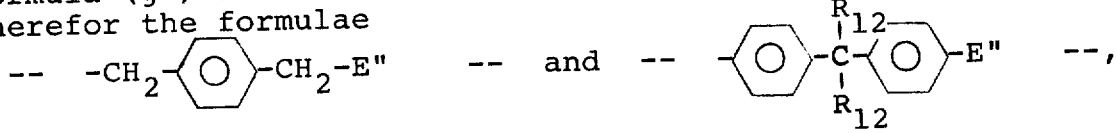

respectively.

UNITED STATES PATENT AND TRADEMARK OFFICE
CERTIFICATE OF CORRECTION

PATENT NO. : USP 4,284,790

DATED : August 18, 1981

INVENTOR(S) : Hans Hinsken, et al.

It is certified that error appears in the above—identified patent and that said Letters Patent is hereby corrected as shown below:

At the top of Column 27; delete the structural formula and substitute therefor

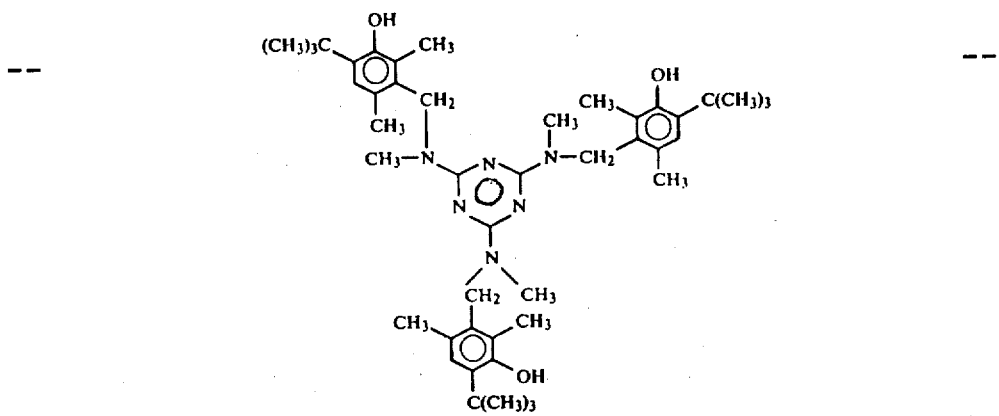

Signed and Sealed this

Twenty-first Day of December 1982

[SEAL]

Attest:

GERALD J. MOSSINGHOFF

Attesting Officer   Commissioner of Patents and Trademarks